(12) United States Patent
Irrgang

(10) Patent No.: US 12,090,258 B2
(45) Date of Patent: Sep. 17, 2024

(54) DIALYSIS MACHINE AND METHOD OF OPERATING A BALANCING CHAMBER SYSTEM OF A DIALYSIS MACHINE

(71) Applicant: Fresenius Medical Care Deutschland GmbH, Bad Homburg (DE)

(72) Inventor: Tobias Irrgang, Aubstadt (DE)

(73) Assignee: FRESENIUS MEDICAS CARE DEUTSCHLAND GMBH, Bad Homburg (DE)

( * ) Notice: Subject to any disclaimer, the term of this patent is extended or adjusted under 35 U.S.C. 154(b) by 436 days.

(21) Appl. No.: 17/625,111

(22) PCT Filed: Jul. 9, 2020

(86) PCT No.: PCT/EP2020/069396
§ 371 (c)(1),
(2) Date: Jan. 6, 2022

(87) PCT Pub. No.: WO2021/005164
PCT Pub. Date: Jan. 14, 2021

(65) Prior Publication Data
US 2022/0257842 A1 Aug. 18, 2022

(30) Foreign Application Priority Data
Jul. 9, 2019 (DE) .................... 10 2019 118 521.1

(51) Int. Cl.
*A61M 1/16* (2006.01)
(52) U.S. Cl.
CPC ................................ *A61M 1/1639* (2014.02)
(58) Field of Classification Search
None
See application file for complete search history.

(56) References Cited

U.S. PATENT DOCUMENTS 4,997,570 A * 3/1991 Polaschegg ............. A61M 1/16
210/123
6,042,784 A * 3/2000 Wamsiedler ............ A61M 1/16
604/4.01

(Continued)

FOREIGN PATENT DOCUMENTS

| DE | 197 08 391 | 10/1998 |
| EP | 3 165 243 | 5/2017 |
| WO | WO 2015/118046 | 8/2015 |

OTHER PUBLICATIONS

Breuch, G. "Balancing in dialysis rats or how do ailance chamber systems work?" Spectrum of the Dialyse & Apharesis dated Sep. 20, 2012.

*Primary Examiner* — Krishnan S Menon
(74) *Attorney, Agent, or Firm* — Jacobson Holman PLLC

(57) ABSTRACT

The present invention relates to a dialysis machine having a dialyzer and having a first balancing chamber and having a second balancing chamber, wherein the first inflows of the first balancing chamber halves are in fluid communication with a source of fresh dialyzate and the first outflows of the first balancing chamber halves are in fluid communication with a dialyzer inflow, and wherein the second inflows of the second balancing chamber halves are in fluid communication with a dialyzer outflow and the second outflows of the second balancing chamber halves are in fluid communication with a drain, wherein a third balancing chamber is provided that has two balancing chamber halves that are separated from one another by a movable wall, wherein each of the balancing chamber halves has a respective inflow and a respective outflow that are each provided with valves that are configured to close or open the respective inflow or outflow, wherein the two inflows are in fluid communication with a source of fresh dialyzate, and wherein the two (Continued)

outflows are in fluid communication with the dialyzer inflow.

14 Claims, 2 Drawing Sheets

(56) References Cited

U.S. PATENT DOCUMENTS

| | | | |
|---|---|---|---|
| 2009/0008306 A1* | 1/2009 | Cicchello | A61M 1/1686 210/103 |
| 2022/0387683 A1* | 12/2022 | Irrgang | A61M 1/1639 |

* cited by examiner

DIALYSIS MACHINE AND METHOD OF OPERATING A BALANCING CHAMBER SYSTEM OF A DIALYSIS MACHINE

The present invention relates to a dialysis machine having a dialyzer and having a first balancing chamber and having a second balancing chamber of which each has at least two first and second balancing chamber halves separated from one another by a movable wall, wherein each first balancing chamber half is provided with a respective first inflow and with a respective first outflow, wherein each second balancing chamber half is provided with a respective second inflow and with a respective second outflow, wherein the inflows and outflows are each provided with valves that are configured to close or to open the respective inflow or outflow, wherein the first inflows of the first balancing chamber halves are in fluid communication with a source of fresh dialyzate and the first outflows of the first balancing chamber halves are in fluid communication with a dialyzer inflow, and wherein the second inflows of the second balancing chamber halves are in fluid communication with a dialyzer outflow and the second outflows of the second balancing chamber halves are in fluid communication with a drain.

Figure 2:
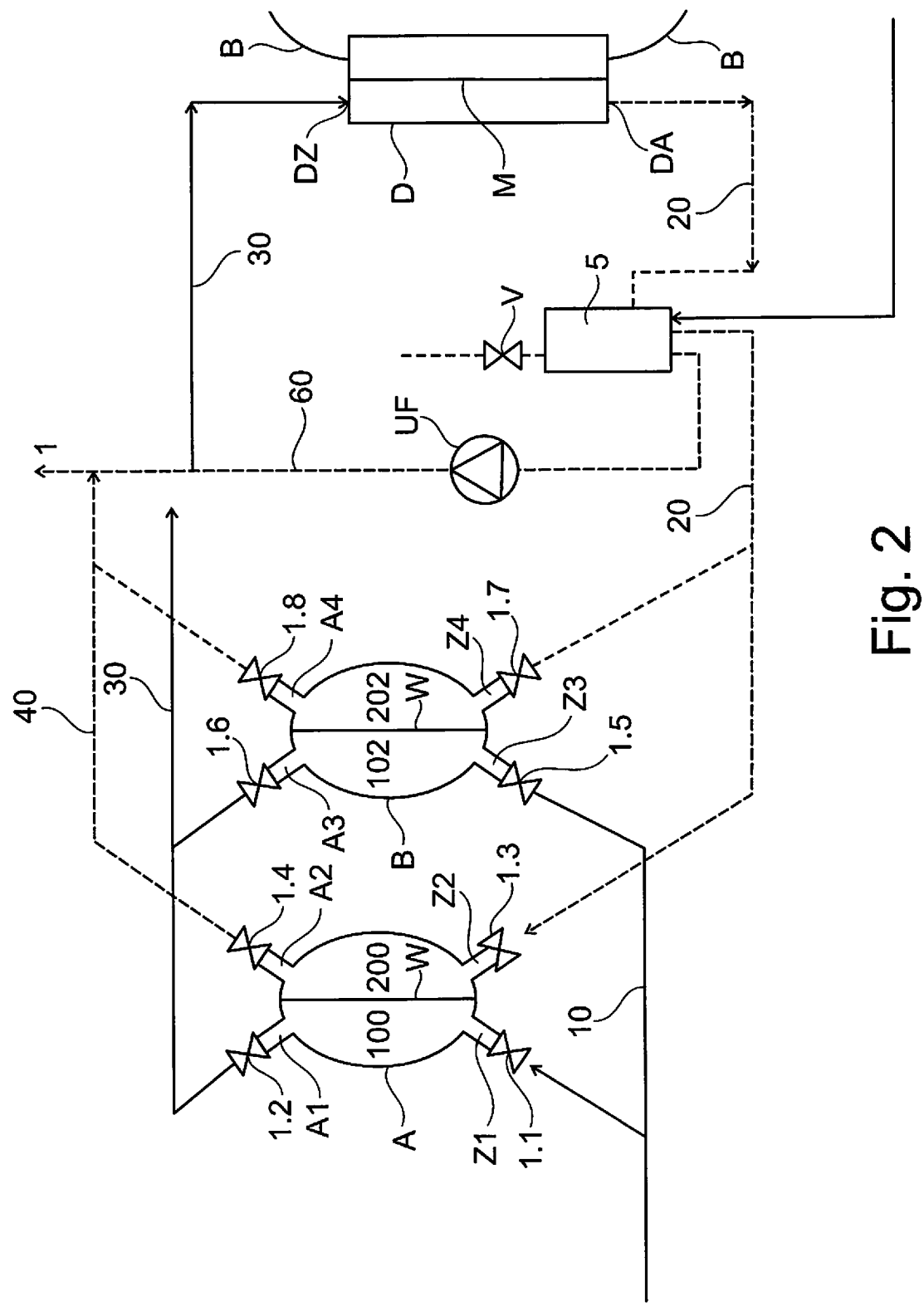

Such a dialysis machine is known from the prior art and is shown by way of example in FIG. 2.

FIG. 2 shows a dialysis machine in the state of "normal" hemodialysis without substituate conveying.

As can be seen from FIG. 2, two balancing chambers A and B are provided of which each has a first balancing chamber half 100, 102 and a second balancing chamber half 200, 202. The balancing chamber halves are each separated from one another by a movable wall W.

It furthermore results from FIG. 2 that each balancing chamber half 100, 200, 102, 202 has a respective first inflow Z1 and Z3 for fresh dialyzate that is supplied via the line 10 and a respective second inflow Z2 and Z4 for consumed dialyzate that is supplied from the dialyzer D via the line 20. The inflows Z1 and Z2 of the first balancing chamber A are closable by means of the valves 1.1 and 1.3; the outflows A1 and A2 of the first balancing chamber A are closable by means of the valves 1.2 and 1.4. The inflows Z3 and Z4 of the second balancing chamber B are closable by means of the valves 1.5 and 1.7 and the outflows A3 and A4 of the second balancing chamber B are closable by means of the valves 1.6 and 1.8.

The lines in which consumed dialyzate is conveyed are shown dashed in the Figures. Lines in which fresh dialyzate is conveyed are shown by solid lines.

The line 30 is in fluid communication with the outflows A1 and A3 and serves the conveying of fresh dialyzate to the dialyzer D or to its inflow DZ. The latter is divided by the membrane M into two or more than two chambers of which one is flowed through by dialyzate and the other is flowed through by blood B. The consumed dialyzate D including the ultrafiltrate moves on the outflow side DA of the dialyzer D into the secondary air separator S that has a valve V for leading off air.

A portion of the consumed dialyzate is conveyed by means of the ultrafiltration pump UF by means of the line 60 from the secondary air separator S into the drain 1. The remaining portion of the consumed dialyzate moves in a cycled manner via the inflows Z2 and Z4 to the two second balancing chamber halves 200, 202 of the balancing chambers A and B.

The line 40 is in fluid communication with the outflows A2 and A4 of the second balancing chamber halves 200, 202 and serves the conveying of consumed dialyzate to the drain 1.

The balanced conveying of the dialyzate is configured as follows in accordance with FIG. 2:

First, fresh dialyzate is conveyed via the line 10 into the first balancing chamber half 100 of the first balancing chamber A. The valve 1.1 is open and the valve 1.2 is closed for this purpose. Consumed dialyzate is simultaneously removed from the second balancing chamber half 200 of the first balancing chamber A via the line 40 into the drain 1 by the wall W moving to the right here. The valve 1.3 is closed and the valve 1.4 is open here. Exactly one balancing chamber volume is thus conveyed, for example 30 ml.

The second balancing chamber B works in a counter-cycle, i.e. valve 1.5 is closed, valve 1.6 is open, valve 1.7 is open, and valve 1.8 is closed. Overall, consumed dialyzate is conveyed from the first balancing chamber A through the first balancing chamber A in this cycle and fresh dialyzate is conveyed out of the second balancing chamber B.

Subsequently, a new cycle of the balancing chamber system takes place in which fresh dialyzate is conveyed from the first balancing chamber half 100 of the first balancing chamber A and consumed dialyzate is conveyed from the second balancing chamber half 202 of the second balancing chamber B.

The above-described procedure is repeated in a constant sequence.

It is always the same amount of fresh dialyzate and consumed dialyzate that is conveyed and exactly balanced.

Due to the removal of fluid from the patient, ultrafiltrate is additionally produced on the side of the consumed dialyzate and is conveyed through the pump UF that is located in the line 60.

Approximately 2 l of ultrafiltrate per patient and a treatment time of approximately 4 h result in a treatment.

The ultrafiltrate amount is controlled via the ultrafiltrate pump UF that removes the ultrafiltrate from the blood of the patient.

The arrangement in accordance with FIG. 2 known from the prior art provides an exact monitoring of the dialysis fluid amounts (fresh and consumed) and of the ultrafiltrate amount. The control of the ultrafiltrate amount is important because a minimum amount has to be ensured to avoid a hyperhydration of the patient and, on the other hand, too fast a removal of fluid can result in circulatory failure.

Provision can be made in accordance with the prior art that an additional dialyzate amount or liquid amount is conveyed via a separate pump (substituate pump), not shown. This is necessary when a larger amount of ultrafiltrate is removed from the blood than was prescribed for the patient. The substituate can then (as a rule) be supplied downstream of the dialyzer. An addition upstream or upstream and downstream of the dialyzer is generally also possible. Substituate amounts between 20 and 40 l per treatment cycle are typical.

This method is called HDF (hemodiafiltration). The HDF mode has the advantage that an increased convective portion can be conveyed via the dialyzer membrane and the medium molecular weight uremic toxins can thus in particular be especially effectively removed that can only be conveyed diffusively over the membrane to a small degree.

In known devices, a further filter for the substituate is required in addition to the substituate pump, said further filter ensuring a germ free filtration of the substitute. This is required because the substitute is directly infused into the patient's blood.

Such an arrangement is thus complicated and expensive.

It is thus the underlying object of the present invention to further develop a dialysis machine of the initially named kind such that it has a design that is as simple as possible.

This object is achieved by a dialysis machine having the features of claim 1. Provision is accordingly made that a third balancing chamber is provided that has two balancing chamber halves that are separated from one another by a movable wall, wherein each of the balancing chamber halves of the third balancing chamber has a respective inflow and a respective outflow, that are each provided with valves that are configured to close or open the respective inflow or outflow, wherein the two inflows are in fluid communication with a source of fresh dialyzate/substitute, and wherein the two outflows are in fluid communication with the dialyzate inflow.

The third balancing chamber is thus not charged by consumed dialyzate. It instead only serves the conveying of fresh dialyzate or substitute.

The third balancing chamber can be controlled such that it works offset in time or simultaneously with the first and second balancing chambers. The simultaneous operation brings about the advantage that the balancing and thus the operation of the dialysis machine can be continued and does not have to be interrupted when substitute i.e. preferably fresh dialysis solution, is supplied to the dialyzer by means of the third balancing chamber.

The third balancing chamber thus serves the conveying of fresh dialyzate or substitute to the dialyzer so that a separate substitute pump can be dispensed with in an advantageous embodiment of the invention.

The fluid amount (e.g. 1 stroke, 30 ml) conveyed continuously or discontinuously from the third balancing chamber serves as the substitute for the patient. The membrane of the dialyzer simultaneously acts as a sterile filter for the substitute so that neither a separate substitute pump nor a separate sterile filter are provided in a preferred embodiment of the invention. Apart from this, no separate tubing kit is required for the substitute.

By switching the valves of the third balancing chamber to and fro, a respective volume of a balancing chamber half can now be conveyed as the substitute into the system circuit.

The two inflows of the third balancing chamber are preferably in fluid communication with the same source of fresh dialyzate as the first inflows of the first and second balancing chambers, i.e. the balancing chambers are fed with fresh dialyzate from the same source. It is generally also conceivable that the inflows of the third balancing chamber are fed from a different source than the first inflows of the second and third balancing chambers so that, for example, a different solution can be used for the substitute than for the dialyzate, In a further embodiment of the invention, the two outflows of the third balancing chamber are in direct fluid communication with the same line leading to the dialyzer inflow as the first outflows of the first and second balancing chambers. The two outflows of the third balancing chamber preferably open into the same line as the first outflows of the first and second balancing chambers.

Provision can furthermore be made that the machine does not have its own substitute pump for conveying a substitution fluid into the blood of the patient. The design of the machines is accordingly simplified. As stated, the third balancing chamber takes over the function of the substitute pump and the dialyzer membrane takes over the function of the sterile filter in this case.

One or both balancing chamber halves of the third balancing chamber can have a smaller volume that the balancing chamber halves of the first and second balancing chambers to achieve a particularly precise metering by means of the third balancing chamber.

Provision can be made to enable a slow metering from the third balancing chamber that a throttle member is arranged upstream and/or downstream of the third balancing chamber, said throttle member being configured to throttle the inward flow and/or the outward flow of fresh dialyzate from the third balancing chamber. The throttle member can e.g. be a diaphragm, a constriction, a valve, etc. The throttle member can be adjustable such that the degree of throttling is changeable or can also be configured as not adjustable.

The dialysis machine can be provided with a control that is configured to carry out the supply of fresh dialyzate from the third balancing chamber to the dialyzer distributed evenly in time or unevenly in time over the treatment duration. An intermittent conveying, a conveying constant in time, or a time variable conveying, e.g. a profiled conveying, from the third balancing chamber are e.g. conceivable.

The dialyzer can, for example, be a high-flux dialyzer or a medium cut-off dialyzer. Filters are called high-flux dialyzers that have an ultrafiltration rate of 20-70 mL/m2*mmHg*h in human blood. In these dialyzers, the substitute supply in accordance with the invention is particularly easy to achieve due to the high water permeability in the full blood. In this respect, substitute amounts of 5 to 25 l per 4 hour treatment are preferably set, particularly preferably 15 to 25 l per 4 hour treatment.

The dialysis machine in accordance with the invention is particularly efficient in medium cut-off dialyzers or protein leaking dialyzers. Such dialyzers have an even higher ultrafiltration rate in full blood than high-flux dialyzers; however, the increased albumin loss that can amount to up to 8 g in a treatment of 4 hours has proved to be disadvantageous. In medium cut-off dialyzers, a substitute supply takes place by uncontrolled back filtration. The substitute amount can be exactly controlled by a dialysis machine in accordance with the invention. Higher substitute amounts are in particular also possible than with a dialysis machine in accordance with the prior art that is operated with a medium cut-off dialyzer. The optimum substitute amount can thus also be provided while taking account of the permitted albumin loss with different hematocrit values of the patient's blood. Substitute amounts of 5-20 l can be set in accordance with the invention with a 4 hour HD treatment. Substitute amounts of 8 to 15 l per 4 hour treatment are preferred.

The present invention further relates to a method of operating a balancing chamber system of a dialysis machine having a first balancing chamber and having a second balancing chamber of which each has at least two first and second balancing chamber halves separated from one another by a movable wall, wherein each first balancing chamber half is provided with a respective first inflow and with a respective first outflow, wherein each second balancing chamber half is provided with a respective second inflow and with a respective second outflow, wherein the inflows and outflows are each provided with valves that are configured to close or to open the respective inflow or outflow, wherein the first inflows of the first balancing chamber halves are in fluid communication with a source of fresh dialyzate and the first outflows of the first balancing chamber halves are in fluid communication with a dialyzer inflow, and wherein the second inflows of the second balancing chamber halves are in fluid communication with a dialyzer outflow and the second outflows of the second balancing chamber halves are in fluid communication with a drain.

Provision is made in accordance with the invention that a third balancing chamber is provided that has two balancing chamber halves that are separated from one another by a movable wall, wherein each of these balancing chamber halves has a respective inflow and a respective outflow that are each provided with valves, wherein the two inflows are in fluid communication with a source of fresh dialyzate, and wherein the two outflows are in fluid communication with the dialyzer inflow, with the valves of the third balancing chamber being operated such that fresh dialyzate is conveyed from the third balancing chamber to the dialyzer inflow.

The term of "dialyzate" that is conveyed by means of the third balancing chamber comprises any desired dialyzate and substituate. It can here be the same dialyzate by which the first and second balancing chambers are charged or it can also be a different solution.

The valves of the third balancing chamber are preferably operated such that a continuous flow of fresh dialyzate results from the third balancing chamber to the dialyzer inflow. A continuous supply of dialyzate or substituate to the dialyzer and thus also to the patient results over the membrane of the dialyzer in this case.

However, the case is also covered by the invention that the third balancing chamber is operated discontinuously.

To achieve a slow metering of substituate in a targeted manner, provision can be made that the supply of fresh dialyzate to the third balancing chamber and/or the removal of fresh dialyzate from the third balancing chamber to the dialyzer inflow is throttled.

A control and evaluation unit can be provided that is configured to operate the third balancing chamber such that the medically prescribed substituate amount is distributed evenly in time over the treatment duration. It is also conceivable that the control and evaluation unit is configured such that the medically prescribed substituate amount is distributed unevenly in time over the treatment duration. It is, for example, conceivable here that the substituate amount is larger at the start of the treatment than at the end of the treatment, that a profiled addition of substituate takes place, etc.

As stated, it is of advantage if no substituate pump is used for the supply of substituate to the patient. Such a substituate pump can be dispensed with since the substituate conveyed by the third balancing chamber is anyway supplied to the patient in part over the membrane of the dialyzer.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Figure 1:
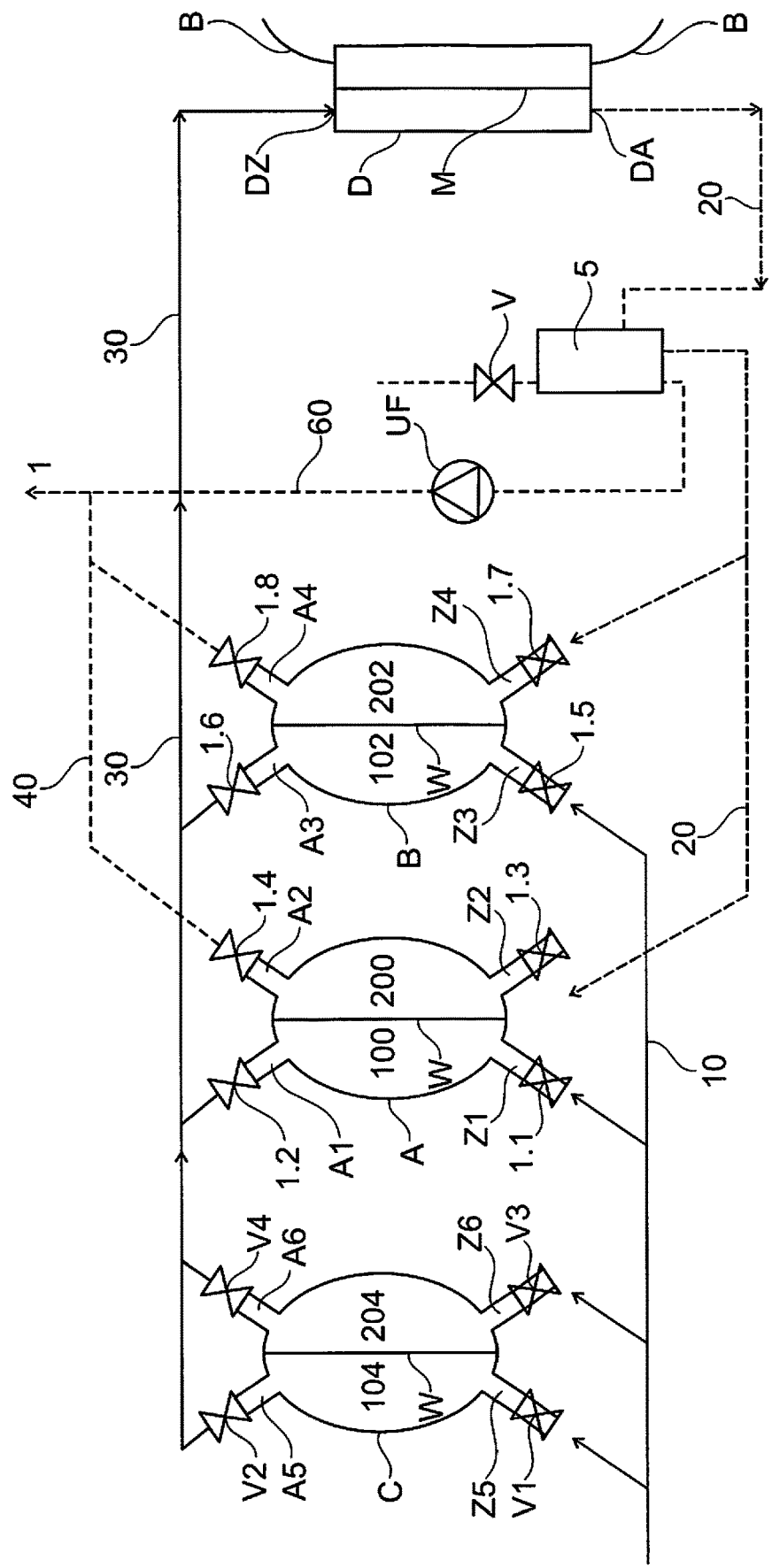

Further details and advantages of the invention will be explained in more detail with reference to an embodiment shown in the drawing.
There are Shown:
  FIG. 1: a schematic view of the dialyzate circuit of a dialysis machine in accordance with the invention; and
  FIG. 2: a schematic view of the dialysis circuit of a dialysis machine in accordance with the prior art.

Elements that are the same or have the same function are marked in FIG. 1 by the same reference numerals as in FIG. 2 so that reference is made accordingly.

The operation of the dialysis machine in accordance with the invention in accordance with FIG. 1 is configured as follows.

The cycled operation of the first and second balancing chambers A, B is configured as described with respect to FIG. 2 so that reference is made accordingly to the statements there.

A third balancing chamber C is connected in parallel with the first and second balancing chambers A, B.

The third balancing chamber has two inflows Z5, Z6 that are in communication with the same line 10 as the inflows Z1 and Z3 of the first and second balancing chambers A, B. Unlike the first and second balancing chambers, the third balancing chamber is charged with fresh dialyzate from the line 10 at both inflows. A supply of consumed dialyzate from the dialyzer to the third balancing chamber does not take place. Accordingly, the third balancing chamber conveys only fresh dialyzate from the outflows A5, A6 to the dialyzer, said fresh dialyzate serving as the substituate for the patient, in that it passes at least in part over the dialyzer membrane M into the blood of the patient. The removal of fresh dialyzate from the third balancing chamber C takes place via the same line as the removal of fresh dialyzate from the first and second balancing chambers. This line leads directly from the respective outlets of the balancing chamber halves to the dialyzer inlet.

The mode of operation of the third balancing chamber otherwise corresponds to that of the first and second balancing chambers, i.e. whereas one balancing chamber half is filled with a corresponding valve switching, the other balancing chamber half is emptied by the displacement of the wall W caused thereby, and vice versa.

The dialyzer membrane simultaneously acts as a sterile filter for the substituate. A sterile filter separately provided for the sterilization of substituate can be dispensed with.

There is the advantage that no separate substituate pump, no separate tubing kit, and no separate sterile filter have to be provided. The third balancing chamber takes over the function of the substituate pump and the dialyzer membrane takes over the function of the sterile filter.

A separate substituate line is preferably also not required since the substituate is conducted to the dialyzer through the same line as the dialyzate that is conveyed through the first and second balancing chambers.

The apparatus can comprise an evaluation and control unit that evenly distributes the medically prescribed substituate amount over the treatment duration.

The apparatus can comprise an evaluation and control unit that unevenly distributes the medically prescribed substituate amount over the treatment duration. This means that, for example, the substituate amount is higher or lower at the start of the treatment than at the end of the treatment.

The apparatus has a particularly good effect when dialyzers are used that are called high-flux dialyzers. Filters are called high-flux dialyzers that have an ultrafiltration rate of 20-70 mL/m$^2$*mmHg*h in human blood.

The apparatus in accordance with the invention is in particular effective in conjunction with a so-called medium cut-off dialyzer. Such a dialyzer is described, for example, in WO 2015/118046 A to which reference is made to this extent. Such dialyzers have an uncontrolled back rinsing of dialyzate into the blood circuit, which is produced by the internal pressure relationships in the dialyzer. These dialyzers may not be operated in HDF mode since the loss of albumin would otherwise become significantly too high.

With the aid of the apparatus in accordance with the invention, operation can now be made in a "controlled substitute mode" with a "normal" machine. The substitute amount can in particular be limited by a skillful program selection to volumes between 2 and 15 l/treatment, preferably to volumes between 5 and 12 l/treatment, further preferably to volumes between 5 and 10 l/treatment.

The invention claimed is:

1. A dialysis machine having a dialyzer (D) and having a first balancing chamber (A) and having a second balancing chamber (B) of which each has at least two first (100, 102) and second balancing chamber halves (200, 202) separated from one another by a movable wall (W), wherein each first balancing chamber half (100, 102) is provided with a respective first inflow (Z1, Z3) and with a respective first outflow (A1, A3), wherein each second balancing chamber half (200, 202) is provided with a respective second inflow (Z2, Z4) and with a respective second outflow (A2, A4), wherein the inflows and outflows (A1-A4, Z1-Z4) are each provided with valves (1.1-1.4; 2.1-2.4) that are configured to close or to open the respective inflow (Z1-Z4) or outflow (A1-A4), wherein the first inflows (Z1; Z3) of the first balancing chamber halves (100; 102) are in fluid communication with a source of fresh dialyzate and the first outflows (A1; A3) of the first balancing chamber halves (100; 102) are in fluid communication with a dialyzer inflow (DZ), and wherein the second inflows (Z2; Z4) of the second balancing chamber halves (200; 202) are in fluid communication with a dialyzer outflow (DA) and the second outflows (A2; A4) of the second balancing chamber halves (200; 202) are in fluid communication with a drain (1), characterized in that a third balancing chamber (C) is provided that has two balancing chamber halves (104; 204) that are separated from one another by a movable wall (W), with each of the balancing chamber halves (104; 204) having a respective inflow (Z5; Z6) and a respective outflow (A5; A6) that are each provided with valves (V1-V4) that are configured to close or to open the respective inflow (Z5; Z6) or outflow (A5; A6), with the two inflows (Z5; Z6) being in fluid communication with a source of fresh dialyzate and with the two outflows (A5; A6) being in fluid communication with the dialyzer inflow (DZ).

2. A dialysis machine in accordance with claim 1, characterized in that the two inflows (Z5; Z6) of the third balancing chamber (C) are in fluid communication with the same source of fresh dialyzate as the first inflows (Z1; Z3) of the first and second balancing chambers (A; B).

3. A dialysis machine in accordance with claim 1, characterized in that the two outflows (A5; A6) of the third balancing chamber (C) are in fluid communication with the same line (30) leading to the dialyzer inflow (DZ) as the first outflows (A2; A4) of the first and second balancing chambers (A; B).

4. A dialysis machine in accordance with claim 1, characterized in that the machine does not have any substitute pump for conveying a substitution solution into the blood of the patient.

5. A dialysis machine in accordance with claim 1, characterized in that the balancing chamber halves (104; 204) of the third balancing chamber (C) have a smaller volume than the balancing chamber halves of the first and second balancing chambers (A; B).

6. A dialysis machine in accordance with claim 1, characterized in that a throttle member is arranged upstream and/or downstream of the third balancing chamber (C), said throttle member being configured to throttle the inward flow and/or the outward flow of fresh dialyzate from the third balancing chamber (C).

7. A dialysis machine in accordance with claim 1, characterized in that a control is provided that is configured to carry out the supply of fresh dialyzate to the dialyzer (D) from the third balancing chamber (C) evenly in time or unevenly in time over a treatment duration.

8. A dialysis machine in accordance with claim 1, characterized in that the dialyzer (D) is a high-flux dialyzer or a medium cut-off dialyzer.

9. A method of operating a balancing chamber system of a dialysis machine having a first balancing chamber (A) and having a second balancing chamber (B) of which each has at least two first (100, 102) and second balancing chamber halves (200, 202) separated from one another by a movable wall (W), wherein each first balancing chamber half (100, 102) is provided with a respective first inflow (Z1, Z3) and with a respective first outflow (A1, A3), wherein each second balancing chamber half (200, 202) is provided with a respective second inflow (Z2, Z4) and with a respective second outflow (A2, A4), wherein the inflows and outflows (A1-A4, Z1-Z4) are each provided with valves (1.1-1.4; 2.1-2.4) that are configured to close or to open the respective inflow (Z1-Z4) or outflow (A1-A4), wherein the first inflows (Z1; Z3) of the first balancing chamber halves (100; 102) are in fluid communication with a source of fresh dialyzate and the first outflows (A1; A3) of the first balancing chamber halves (100; 102) are in fluid communication with a dialyzer inflow (DZ), and wherein the second inflows (Z2; Z4) of the second balancing chamber halves (200; 202) are in fluid communication with a dialyzer outflow (DA) and the second outflows (A2; A4) of the second balancing chamber halves (200; 202) are in fluid communication with a drain (1), characterized in that a third balancing chamber (C) is provided that has two balancing chamber halves (104; 204) that are separated from one another by a movable wall (W), with each of the balancing chamber halves (104; 204) having a respective inflow (Z5; Z6) and a respective outflow (A5; A6) that are each provided with valves (V1-V4), with the two inflows (Z5; Z6) being in fluid communication with a source of fresh dialyzate and with the two outflows (A5; A6) being in fluid communication with the dialyzer inflow (DZ), with the valves (V1-V4) being operated such that fresh dialyzate is conveyed from the third balancing chamber (C) to the dialyzer inflow (DZ).

10. A method in accordance with claim 9, characterized in that the valves (V1-V4) of the third balancing chamber are operated such that a continuous flow of fresh dialyzate results from the third balancing chamber (C) to the dialyzer inflow (DZ).

11. A method in accordance with claim 9, characterized in that the third balancing chamber (C) is operated continuously or discontinuously.

12. A method in accordance with claim 9, characterized in that the supply of fresh dialyzate to the third balancing chamber (C) and/or the removal of fresh dialyzate from the third balancing chamber (C) to the dialyzer inflow is throttled.

13. A method in accordance with claim 9, characterized in that the third balancing chamber (C) is operated such that the conveying rate of fresh dialyzate from the third balancing chamber (C) to the dialyzer inflow is constant or varied over a treatment duration.

14. A method in accordance with claim 9, characterized in that no substituate pump is used to supply substituate to the patient.

\* \* \* \* \*

UNITED STATES PATENT AND TRADEMARK OFFICE
CERTIFICATE OF CORRECTION

| | | |
|---|---|---|
| PATENT NO. | : 12,090,258 B2 | Page 1 of 1 |
| APPLICATION NO. | : 17/625111 | |
| DATED | : September 17, 2024 | |
| INVENTOR(S) | : Tobias Irrgang | |

It is certified that error appears in the above-identified patent and that said Letters Patent is hereby corrected as shown below:

On the Title Page

Item (73) Assignee: please change "Fresenius Medicas Care Deutschland GmbH" to -- Fresenius Medical Care Deutschland GmbH --.

Signed and Sealed this
Thirty-first Day of December, 2024

Derrick Brent
*Acting Director of the United States Patent and Trademark Office*